United States Patent
Belthangady et al.

(10) Patent No.: US 11,369,269 B2
(45) Date of Patent: Jun. 28, 2022

(54) SHORT-WAVE INFRARED AND 3D TOPOGRAPHIC IMAGER

(71) Applicant: Verily Life Sciences LLC, South San Francisco, CA (US)

(72) Inventors: Chinmay Belthangady, Livermore, CA (US); James Polans, San Francisco, CA (US); Daniele Piponi, Oakland, CA (US); Eden Rephaeli, Oakland, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 582 days.

(21) Appl. No.: 16/255,168

(22) Filed: Jan. 23, 2019

(65) Prior Publication Data
US 2019/0246905 A1 Aug. 15, 2019

Related U.S. Application Data

(60) Provisional application No. 62/630,336, filed on Feb. 14, 2018.

(51) Int. Cl.
*A61B 5/00* (2006.01)
*G06T 7/521* (2017.01)
*G01N 21/47* (2006.01)

(52) U.S. Cl.
CPC .......... *A61B 5/0062* (2013.01); *A61B 5/0035* (2013.01); *A61B 5/0073* (2013.01);
(Continued)

(58) Field of Classification Search
CPC .............................. A61B 5/0062; G06T 7/521
See application file for complete search history.

(56) References Cited

U.S. PATENT DOCUMENTS

2003/0139667 A1   6/2003   Hewko et al.
2005/0273011 A1   12/2005   Hattery et al.
(Continued)

FOREIGN PATENT DOCUMENTS

WO   2013/160780 A1   10/2013
WO   2017176301        10/2017

OTHER PUBLICATIONS

Almaz et al., "Influence of stains on lesion contrast in the pits and fissures of tooth occlusal surfaces from 800-1600-nm", Proceedings of SPIE—the International Society for Optical Engineering. vol. 9692. NIH Public Access, 2016, 11 pages.
(Continued)

*Primary Examiner* — Jason M Ip
(74) *Attorney, Agent, or Firm* — Kilpatrick Townsend & Stockton LLP

(57) ABSTRACT

Systems and methods for acquiring images of a sample are provided. According to an aspect of the invention, a system includes a first light source that emits first light having a first wavelength as a temporally continuous beam; a second light source that emits second light having a second wavelength as a temporally modulated beam; and a scanning mirror that raster scans the first light across a sample during a raster scan period, and projects a structured light pattern of the second light onto the sample during the raster scan period. A first image of the sample is generated from at least a portion of the first light that is backscattered from the sample during the raster scan period, and a second image of the sample is generated from at least a portion of the second light that is backscattered from the sample during the raster scan period.

20 Claims, 7 Drawing Sheets

(52) U.S. Cl.
CPC ....... *A61B 5/0075* (2013.01); *G01N 21/4795* (2013.01); *G06T 7/521* (2017.01); *A61B 5/0088* (2013.01); *G01N 2021/4709* (2013.01); *G06T 2207/10048* (2013.01); *G06T 2207/30036* (2013.01)

(56) References Cited

U.S. PATENT DOCUMENTS

| | | | | |
|---|---|---|---|---|
| 2009/0262363 | A1* | 10/2009 | Keshavmurthy | G01B 11/2509 356/511 |
| 2012/0218464 | A1* | 8/2012 | Ben-Moshe | G02B 26/0833 348/369 |
| 2016/0327779 | A1* | 11/2016 | Hillman | G02B 21/0052 |

OTHER PUBLICATIONS

Carr et al., "Using the shortwave infrared to image middle ear pathologies", Proceedings of the National Academy of Sciences 113.36 (2016): pp. 9989-9994.
Chung et al., "Multispectral near-IR reflectance and transillumination imaging of teeth", Biomedical optics express 2.10 (2011): pp. 2804-2814.
Geng, "Structured-light 3D surface imaging: a tutorial", Advances in Optics and Photonics 3.2 (2011): pp. 128-160.
Huang et al., "Fast three-step phase-shifting algorithm", Applied optics 45.21, Jul. 20, 2006, pp. 5086-5091.
Kuruvilla et al., "Automated diagnosis of otitis media: vocabulary and grammar", Journal of Biomedical Imaging 2013 (2013): 27, 15 pages.
Zakian et al., "Near-infrared hyperspectral imaging of teeth for dental caries detection", Journal of Biomedical Optics 14.6 (2009): p. 064047-064047.
Fried et al., "Imaging early demineralization on tooth occlusional surfaces with a high definition InGaAs camera", design for manufacturability through design-process integration III, vol. 8566, Mar. 25, 2013, 8 pages.
Geng, "Structured-light 3D surface imaging: a tutorial", Advances in Optics and Photonics, vol. 3, No. 2, Mar. 31, 2011, pp. 128-160.
International Application No. PCT/US2019/014721, "International Search Report and Written Opinion", dated Apr. 18, 2019, 11 pages.

* cited by examiner

SHORT-WAVE INFRARED AND 3D TOPOGRAPHIC IMAGER

CROSS-REFERENCE TO RELATED APPLICATION

This application claims priority under 35 U.S.C. § 119 to U.S. Provisional Patent Application No. 62/630,336, filed on Feb. 14, 2018, the contents of which are hereby incorporated by reference in their entirety for all purposes.

BACKGROUND

Imaging in the short-wave infrared (SWIR) region of the light spectrum, defined herein as light having wavelengths between 900 nm and 1700 nm, is of value for early detection or accurate diagnosis of many diseases. This is because there is reduced photon scatter from tissue at these wavelengths. Furthermore, several absorption peaks from tissue components such as water and lipids lie in this region of the light spectrum, enabling high specificity for detection of these tissue components. Applications of SWIR biomedical imaging include the early detection of carious lesions in teeth and the detection of fluid accumulation in the middle ear during Otitis Media infections. However, SWIR imagers for biomedical applications typically capture images with an InGaAs multi-pixel focal plane array detector, which tends to be very expensive, relatively large, and suffer from a large dead pixel count.

The acquisition of three-dimensional (3D) topographic data is also of value for biomedical imaging. For example, the degree to which the tympanic membrane bulges can help differentiate between Otitis Media with Effusion (OME) and Acute Otitis Media (AOM). In both cases fluid accumulates in the middle ear, but a pronounced bulge of the tympanic membrane is seen only in AOM. However, structured light 3D imagers typically use a video projector and a camera separated by a baseline distance for triangulation-based depth determination. These imagers are not well suited for the space-constrained settings that are often encountered in biomedical imaging.

SWIR imaging provides the ability to see deeply into tissue, observe fluid build-up, and contrast differences between different types of tissue. 3D topographic imaging shows the shape or contour of biological features, and illustrates height differences within a sample. Therefore, it would be advantageous to develop an integrated imaging system that is capable of acquiring SWIR and 3D topographic images of a sample.

SUMMARY

Exemplary embodiments of the invention provide an imaging system that is configured to acquire SWIR and 3D topographic images of a sample. The system may also acquire color images of the sample. The system may acquire the SWIR, 3D topographic, and color images simultaneously or nearly simultaneously.

According to an aspect of the invention, a system includes a first light source that is configured to emit first light having a first wavelength as a temporally continuous beam; a second light source that is configured to emit second light having a second wavelength as a temporally modulated beam; and a scanning mirror that is configured to raster scan the first light across a sample during a raster scan period, and project a structured light pattern of the second light onto the sample during the raster scan period. The system also includes a photodetector that is configured to receive at least a portion of the first light that is backscattered from the sample during the raster scan period, and a camera that is configured to receive at least a portion of the second light that is backscattered from the sample during the raster scan period. Further, the system includes one or more processors that are configured to generate a first image of the sample from the at least the portion of the first light that is backscattered from the sample during the raster scan period, generate a second image of the sample from the at least the portion of the second light that is backscattered from the sample during the raster scan period, wherein the second image of the sample is a three-dimensional topographic image of the sample, and output the first image of the sample and the second image of the sample.

The first wavelength may be between 900 nm and 1700 nm, and the second wavelength may be between 380 nm and 900 nm. The system may also include a combiner that is configured to combine the first light and the second light along a single path, and to direct the first light and the second light to the scanning mirror.

The system may also include a third light source that is configured to project white light onto the sample before or after the raster scan period. The camera may be further configured to receive at least a portion of the white light that is backscattered from the sample before or after the raster scan period. The processor may be further configured to generate a third image of the sample from the at least the portion of the white light that is backscattered from the sample before or after the raster scan period, wherein the third image of the sample is a color image of the sample.

The structured light pattern of the second light may include a Gray code pattern. Alternatively, the structured light pattern of the second light may include three sinusoidal patterns that are sequentially projected onto the sample and are phase shifted by 120 degrees relative to each other. In this embodiment, the one or more processors may be further configured to calculate a third image of the sample from images of the sample generated by the sinusoidal patterns. Here the third image of the sample is a color image of the sample. In addition, the one or more processors may be further configured to calculate the second image of the sample from images of the sample generated by the sinusoidal patterns.

The system may also include a display that is configured to show the first image of the sample and the second image of the sample. The photodetector may be a single-pixel InGaAs photodetector.

According to another aspect of the invention, a method includes emitting first light having a first wavelength as a temporally continuous beam; emitting second light having a second wavelength as a temporally modulated beam; raster scanning the first light across a sample during a raster scan period; projecting a structured light pattern of the second light onto the sample during the raster scan period; receiving, by a photodetector, at least a portion of the first light that is backscattered from the sample during the raster scan period; generating a first image of the sample from the at least the portion of the first light that is backscattered from the sample during the raster scan period; receiving, by a camera, at least a portion of the second light that is backscattered from the sample during the raster scan period; generating a second image of the sample from the at least the portion of the second light that is backscattered from the sample during the raster scan period, wherein the second image of the sample is a three-dimensional topographic image of the sample; and outputting the first image of the sample and the second image of the sample.

The first wavelength may be between 900 nm and 1700 nm, and the second wavelength may be between 380 nm and 900 nm. The method may also include combining the first light and the second light along a single path, and subsequently directing the first light and the second light to a scanning mirror.

The method may also include projecting white light onto the sample before or after the raster scan period; receiving, by the camera, at least a portion of the white light that is backscattered from the sample before or after the raster scan period; and generating a third image of the sample from the at least the portion of the white light that is backscattered from the sample before or after the raster scan period, wherein the third image of the sample is a color image of the sample.

The structured light pattern of the second light may include a Gray code pattern. Alternatively, the structured light pattern of the second light may include three sinusoidal patterns that are sequentially projected onto the sample and are phase shifted by 120 degrees relative to each other. In this embodiment, the method may also include calculating a third image of the sample from images of the sample generated by the sinusoidal patterns, wherein the third image of the sample is a color image of the sample. Further, the second image of the sample may be calculated from images of the sample generated by the sinusoidal patterns.

The method may also include displaying the first image of the sample and the second image of the sample. The photodetector may be a single-pixel InGaAs photodetector.

Other objects, advantages, and novel features of the present invention will become apparent from the following detailed description of the invention when considered in conjunction with the accompanying drawings.

BRIEF DESCRIPTION OF THE DRAWINGS

The present disclosure is described in conjunction with the appended figures.

DETAILED DESCRIPTION

Exemplary embodiments of the invention use a scanning microelectromechanical systems (MEMS) mirror and a single (or multiple) InGaAs photodiode for capturing SWIR images of a sample. The same scanning MEMS mirror is used to project a structured light pattern of visible or near-infrared (NIR) light onto the sample for capturing 3D topographic images of the sample. As defined herein, visible light has a wavelength between 380 nm and 700 nm, and NIR light has a wavelength between 700 nm and 900 nm.

Figure 1:
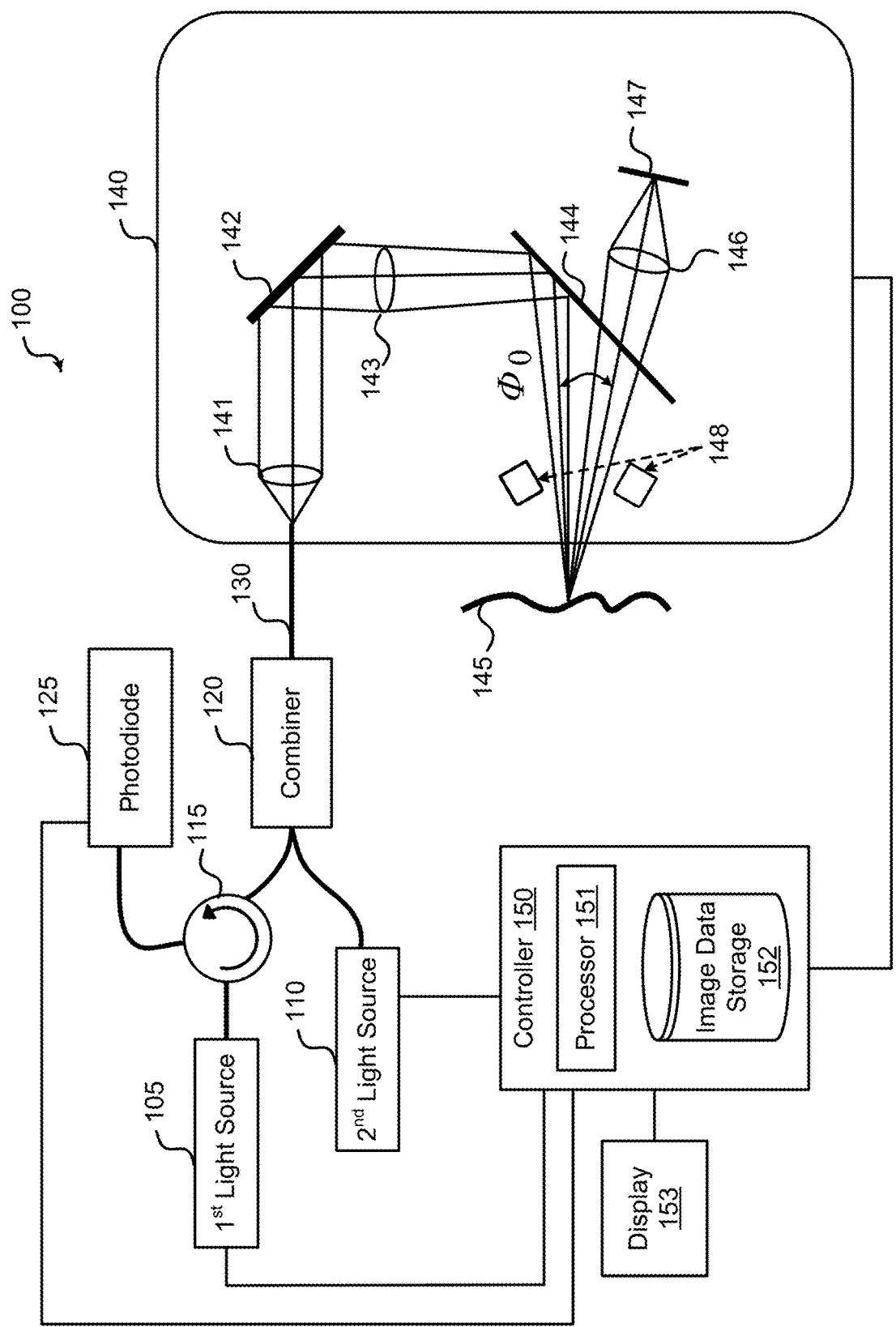
FIG. 1 shows a block diagram of an imaging system according to exemplary embodiments of the invention.

FIG. 1 shows a block diagram of an imaging system 100 according to exemplary embodiments of the invention. A first light source 105 is configured to emit first light having a first wavelength in the SWIR region of the spectrum. For example, the first light source 105 may be a laser that includes a single fiber-coupled illumination source such as a diode laser, or a superluminescent diode that emits light at a single wavelength or multiple wavelengths whose outputs have been combined using a wavelength-division multiplexer (WDM) or a dichroic beam splitter. Alternately the first light source 105 may be a swept frequency laser emitting a wavelength that can be tuned in a certain range within the SWIR region. The first light source 105 is configured to output a temporally continuous beam of light. The output of the first light source 105 may be sent through a circulator 115. Alternatively the circulator 115 may be replaced by a 2×2 fiber coupler, a double-clad-fiber coupler, or a free-space beamsplitter. The output of the first light source 105 is then sent to one input of a combiner 120, such as a WDM or a dichroic beamsplitter.

A second light source 110 is configured to emit second light having a second wavelength in the visible or NIR region of the spectrum. The second light source 110 may be a laser emitting a wavelength that is chosen to coincide with a region of high quantum efficiency of the color camera 147. As discussed in further detail below, the second light source 110 is configured to output a temporally modulated beam of light. The output of the second light source 110 is sent to a second input of the combiner 120. The combiner 120 combines light from the first light source 105 and the second light source 110, and sends the combined light to a scan head 140 via a fiber umbilicus 130.

Within the scan head 140, the combined light is collimated by a collimating optic 141, such as a mirror or a lens, and directed onto a scanning MEMS mirror 142. The scanning MEMS mirror 142 may have a diameter between approximately 0.8 mm and approximately 2.4 mm, such as approximately 1 mm. A focusing optic 143, such as a mirror or a lens, focuses the combined light onto a sample 145 via a beamsplitter 144, such as a 50:50 beamsplitter. Each of the collimating optic 141 and the focusing optic 143 may be a single optical element or a set of optical elements that are designed to maximize imaging performance.

To form a SWIR image, at least a portion of the first light that is diffusely backscattered from the sample 145 is collected by the focusing lens 143 and sent back through the combiner 120, which transmits the first light and directs the first light to an InGaAs photodiode 125 via the circulator 115. The photodetector signal is digitized by an analog-to-digital converter and recorded. The recorded signal is assigned to the pixel position corresponding to the position of the scanning MEMS mirror 142 by a processor 151, and may be shown on a display 153, such as a computer screen.

To form a 3D topographic image, at least a portion of the second light that is diffusely backscattered from the sample 145 is transmitted through the beamsplitter 144 and imaged onto the color camera 147 by an imaging lens 146. The imaging lens 146 may be a single optical element or a set of optical elements that are designed to maximize imaging performance. The optical axis of the color camera 147 may be slightly offset from the optical axis of the scanning path of the scanning MEMS mirror 142 by an angle of $\phi_0$, such as between 15° and 20°, to provide the triangulation offset. The baseline distance b for triangulation is calculated using the cosine rule as:

$$b=\sqrt{c^2+s^2-2*c*s\cos\phi_0} \quad (1)$$

Here c is the distance between the image plane and the entrance pupil of the color camera 147 and s is the distance between the image plane and the entrance pupil of the scanning MEMS mirror 142. The color camera 147 may be a silicon-based visible-light camera without an IR-cut filter. The color camera 147 may have sufficient quantum efficiency in the visible or NIR to be able to detect the second light from the second light source 110.

The scan head 140 may also include a plurality of white-light LEDs 148 that are arranged in a configuration to provide uniform illumination of the sample 145. The color camera 147 may acquire a color image of the sample 145 while the white-light LEDs 148 are turned on and the second light source 110 is turned off.

The SWIR image, the 3D topographic image, and/or the color image may be stored in image data storage 152. The images may also be output, such as to the display 153, and shown on the display 153. The images may be overlaid on each other or shown separately. Further, the images may be provided to an image diagnosis program.

Figure 2:
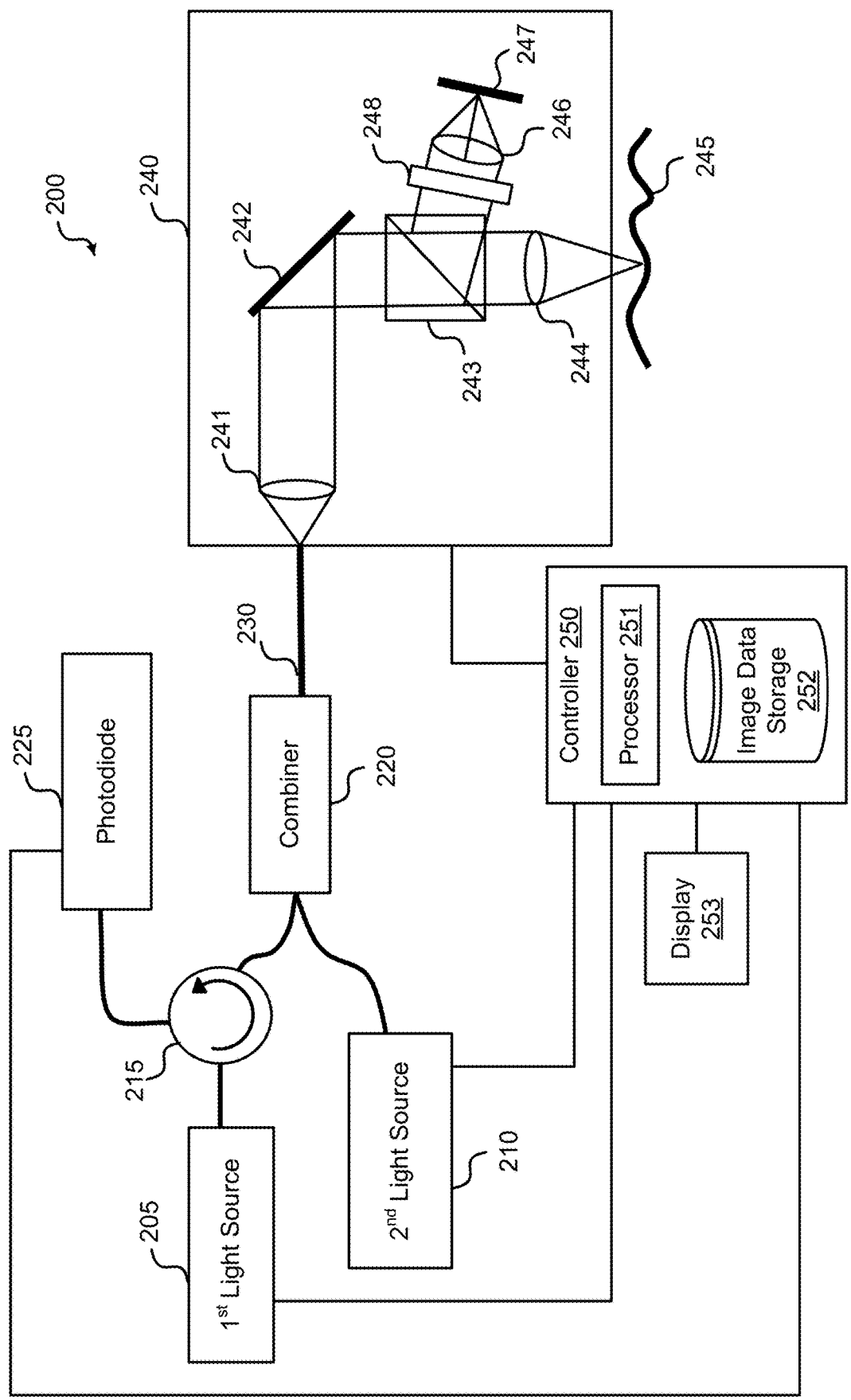
FIG. 2 shows a block diagram of another imaging system according to exemplary embodiments of the invention.

FIG. 2 shows a block diagram of another imaging system 200 according to exemplary embodiments of the invention. As shown in FIG. 2, a first light source 205 is configured to emit first light having a first wavelength in the SWIR region of the spectrum. For example, the first light source 205 may be a laser that includes a single fiber-coupled illumination source such as a diode laser, or a superluminescent diode that emits light at a single wavelength or multiple wavelengths whose outputs have been combined using a wavelength-division multiplexer (WDM) or a dichroic beam splitter. Alternately the first light source 205 may be a swept frequency laser whose wavelength can be tuned in a certain range within the SWIR region. The first light source 205 is configured to output a temporally continuous beam of light. The output of the first light source 205 may be sent through a circulator 215. Alternatively the circulator 215 may be replaced by a 2×2 fiber coupler, a double-clad-fiber coupler, or a free-space beam splitter. The output of the first light source 205 is then sent to one input of a combiner 220, such as a WDM or a dichroic beamsplitter.

As shown in FIG. 2, a second light source 210 is configured to emit second light having a second wavelength in the visible or NIR region of the spectrum. The second light source 210 may include red, green, and blue lasers that are combined via dichroic mirrors or WDMs. Alternatively, the second light source 210 may include a single-wavelength laser, in which case a monochrome image would be obtained instead of a full color image. As discussed in further detail below, the second light source 210 is configured to output a temporally modulated beam of light. The output of the second light source 210 is sent to a second input of the combiner 220. The combiner 220 combines light from the first light source 205 and the second light source 210, and sends the combined light to a scan head 140 via a fiber umbilicus 230.

Within the scan head 240, the combined light is collimated by a collimating optic 241, such as a mirror or a lens, and directed onto a scanning MEMS mirror 242. The scanning MEMS mirror 242 may have a diameter of approximately 1 mm. A focusing optic 244, such as a mirror or a lens, focuses the combined light onto a sample 245 via a beamsplitter 243, such as a 50:50 beamsplitter. Each of the collimating optic 241 and the focusing optic 243 may be a single optical element or a set of optical elements that are designed to maximize imaging performance.

To form a SWIR image, at least a portion of the first light that is diffusely backscattered from the sample 245 is collected by the focusing lens 244 and sent back through the combiner 220, which transmits the first light and directs the first light to an InGaAs photodiode 225 via the circulator 215. The photodetector signal is digitized by an analog-to-digital converter and recorded. The recorded signal is assigned to the pixel position corresponding to the position of the scanning MEMS mirror 242 by a processor 251, and may be shown on a display 253, such as a computer screen.

To form a 3D topographic image, at least a portion of the second light that is diffusely backscattered from the sample 245 is reflected by the beamsplitter 243 and imaged onto the color camera 247 by an imaging lens 246. The imaging lens 246 may be a single optical element or a set of optical elements that are designed to maximize imaging performance. A short-pass filter 248 rejects the SWIR light and transmits the visible or NIR light. The optical axis of the color camera 247 may be slightly offset from the optical axis of the scanning path of the scanning MEMS mirror 242 by an angle of $\phi_0$, such as between 15° and 20°, to provide the triangulation offset. The baseline distance b for triangulation is calculated using the cosine rule according to equation (1) above. Here c is the distance between the image plane and the entrance pupil of the color camera 247 and s is the distance between the image plane and the entrance pupil of the scanning MEMS mirror 242.

The SWIR image, the 3D topographic image, and/or the color image may be stored in image data storage 252. The images may also be output, such as to the display 253, and shown on the display 253. The images may be overlaid on each other or shown separately. Further, the images may be provided to an image diagnosis program.

Figure 3:
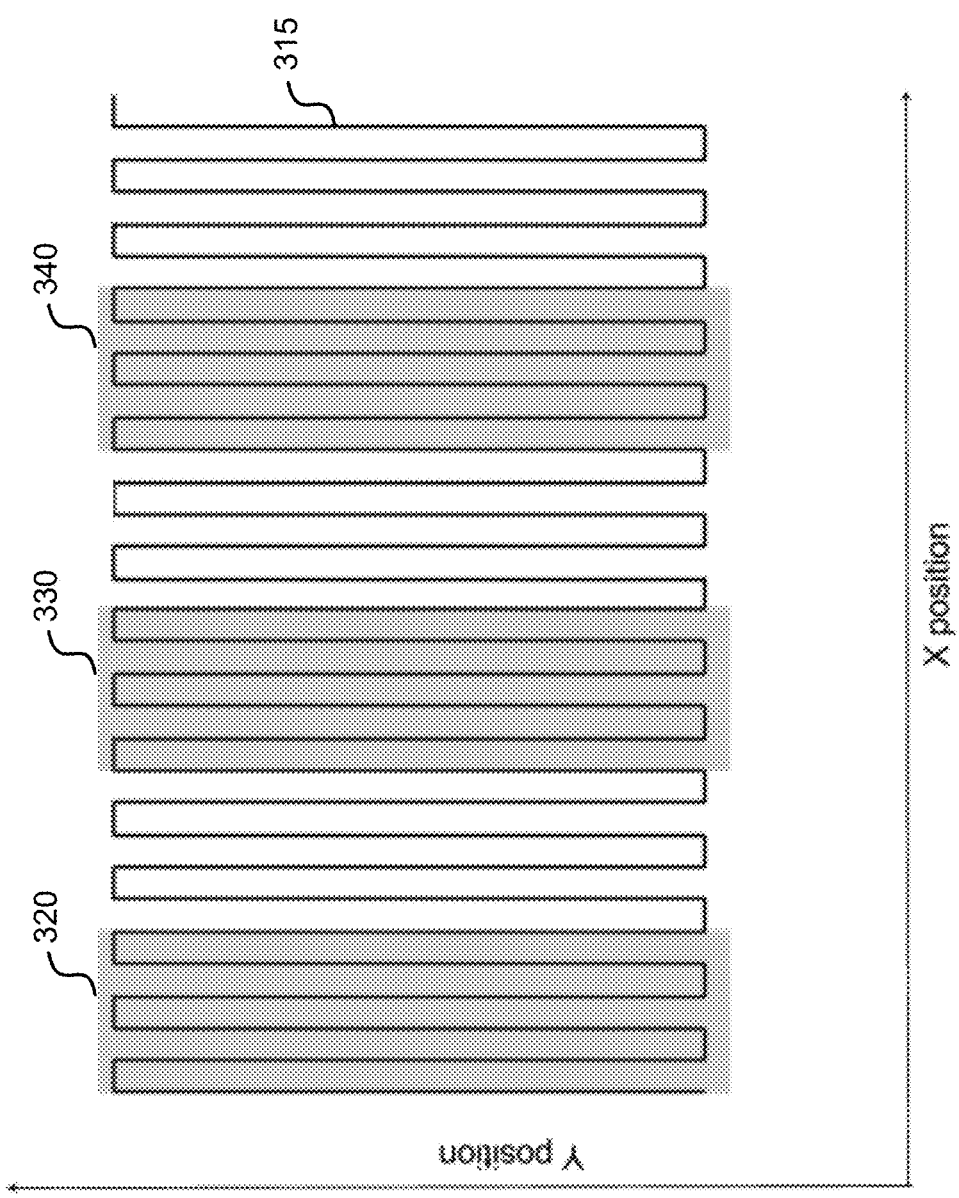
FIG. 3 shows a diagram of a sample illumination pattern according to exemplary embodiments of the invention.

FIG. 3 shows a diagram of a sample illumination pattern according to exemplary embodiments of the invention. The following description of FIG. 3 refers to the imaging system 100 shown in FIG. 1, but a similar description also applies to the imaging system 200 shown in FIG. 2. As discussed above, the first light source 105 is configured to output a temporally continuous beam of light. The controller 150 instructs the scanning MEMS mirror 142 to form a raster scan pattern 315 on the sample 145 with the first light from the first light source 105. The raster scan frequency may be adjusted based on the physical characteristics of the scanning MEMS mirror 142 and/or the maximum frame rate of the color camera 147. FIG. 3 shows an example of a single raster scan period.

The controller 150 also instructs the second light source 110 to turn on and off during the raster scan period, such that the second light source 110 forms a structured light pattern of the second light on the sample 145. In the example shown in FIG. 3, the structured light pattern from the second light source 110 includes several stripes 320, 330, and 340 that overlap with sections of the raster scan pattern 315. The stripes 320, 330, and 340 are formed during times when the second light source 110 is turned on. The second light source may be turned on and off in a square wave pattern or modulated sinusoidally during the raster scan period.

In some embodiments, such as the system 100 shown in FIG. 1, the stripes 320, 330, and 340 shown in FIG. 3 may encode a Gray code. During each raster scan period, a different Gray code may be projected and an image of the sample 145 may be captured. If a number n of Gray code patterns are projected, 3D information can be reconstructed via $2^n$ stripe regions on the sample 145.

Figure 4:
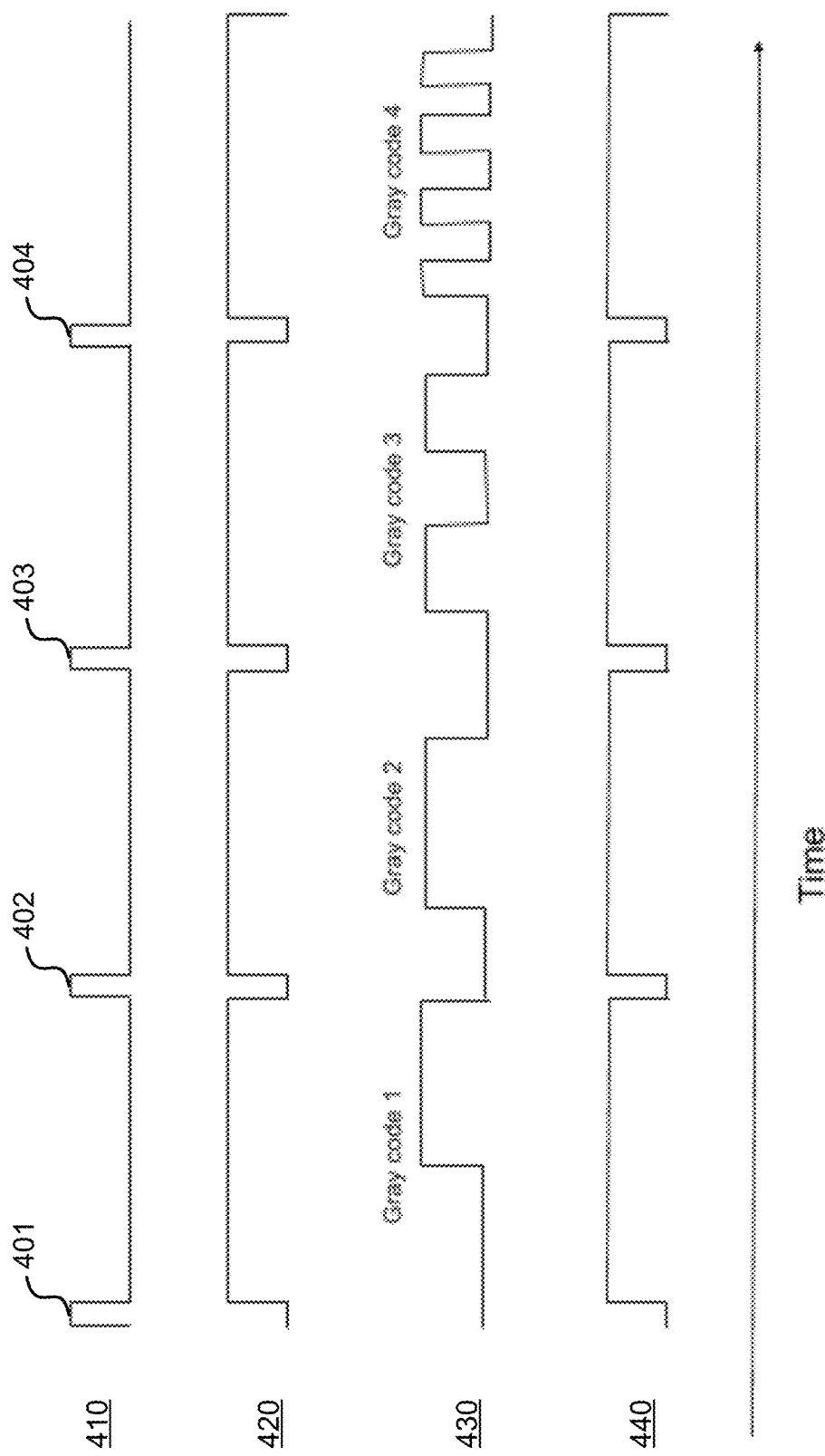
FIG. 4 shows an example of a timing diagram for generating a sample illumination pattern according to exemplary embodiments of the invention.

FIG. 4 shows an example of a timing diagram for generating a sample illumination pattern according to exemplary embodiments of the invention. As shown in FIG. 4, the controller 150 uses a start trigger 410 to control the components within the system 100. Specifically, the start trigger 410 instructs the scanning MEMS mirror 142 to start raster scanning the sample 145 and instructs the first light source 105 to begin emitting first light at the end of a first pulse 401 from the start trigger 410. The first light source 105 then emits first light continuously during each raster scan period, turns off at the beginning of a second pulse 402 from the start trigger 410, and turns on again at the end of the second pulse 402 from the start trigger 410. This causes a pattern 420 of first light to be generated by the first light source 105.

The controller 150 also instructs the second light source 110 to emit a modulated pattern 430 of second light via the start trigger 410. More specifically, the controller 150 instructs the second light source 110 to emit second light having different Gray codes that coincide with pulses from the start trigger 410. For example, as shown in FIG. 4, second light having Gray code 1 is emitted after the first pulse 401, second light having Gray code 2 is emitted after the second pulse 402, second light having Gray code 3 is emitted after the third pulse 403, and second light having Gray code 4 is emitted after the fourth pulse 404. In this manner, different Gray code patterns having different spatial frequencies may be emitted by the second light source 110 during each raster scan period.

In addition, the controller 150 instructs a shutter of the color camera 147 to open at the end of the first pulse 401 from the start trigger 410. The controller 150 instructs the shutter to remain open during the raster scan period, close at the beginning of the second pulse 402 from the start trigger 410, and open again at the end of the second pulse 402 from the start trigger 410. This forms a camera shutter pattern 440 that allows the color camera 147 to acquire a raw image during each raster scan period. As discussed in further detail below, this raw image is used to generate a 3D topographic image of the sample 145.

In order to capture a color image of the sample 145, the controller 150 may instruct the white-light LEDs 148 to turn on while the first light source 105 and the second light source 110 are turned off. For example, to capture a color image of the sample 145 after the first raster scan period, the white-light LEDs 148 may be turned on after the beginning of the second pulse 402, and turned off before the end of the second pulse 402. The shutter of the color camera 147 may be opened during this time to acquire the color image of the sample 145. At least a portion of the white light that is backscattered from the sample 145 is received by the color camera 147 and used to generate the color image.

Figure 5:
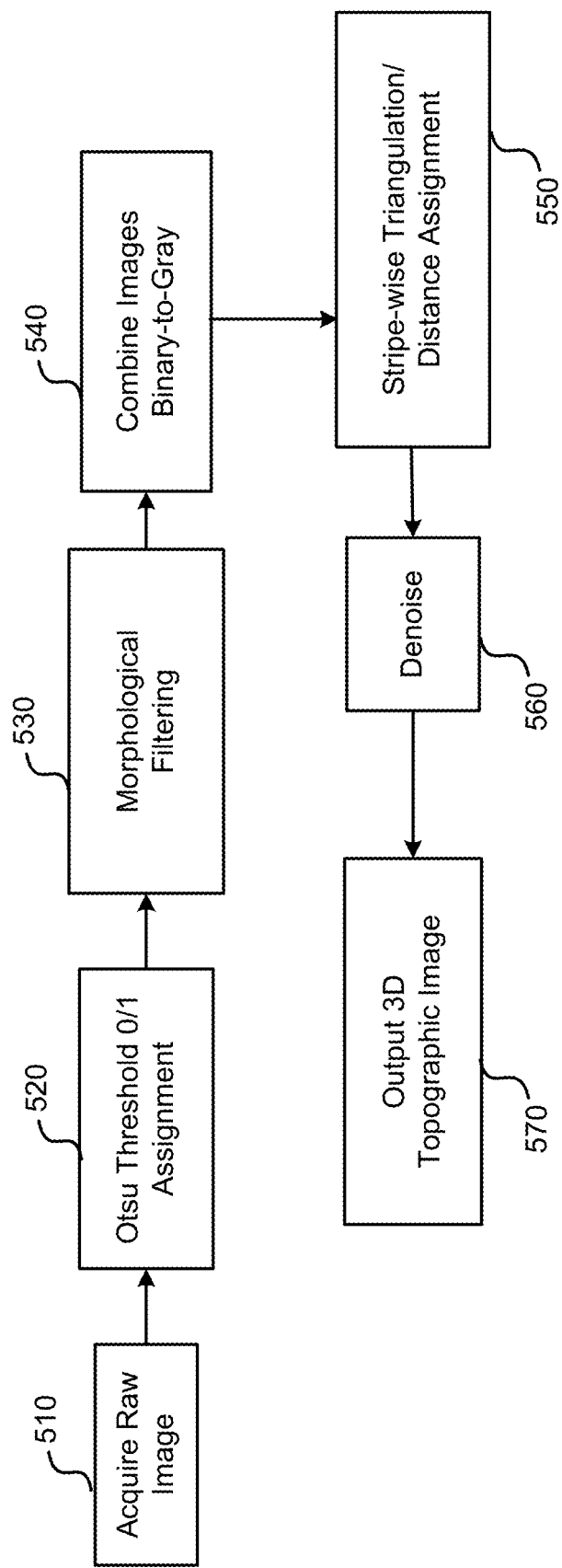
FIG. 5 shows a flowchart of a method for generating a 3D topographic image according to exemplary embodiments of the invention.

FIG. 5 shows a flowchart of a method for generating a 3D topographic image according to exemplary embodiments of the invention. This method may be used in conjunction with the system 100 shown in FIG. 1. A raw image of the structured light pattern of the second light on the sample 145 is acquired by the color camera 147 at 510. An Otsu threshold is applied to the raw image with a 0/1 assignment at 520. Morphological filtering is then performed at 530, and the resulting images are combined to convert the images from binary to grayscale at 540. A stripe-wise triangulation distance assignment is performed at 550. After denoising at 560, a 3D topographic image is output at 570.

Figure 6:
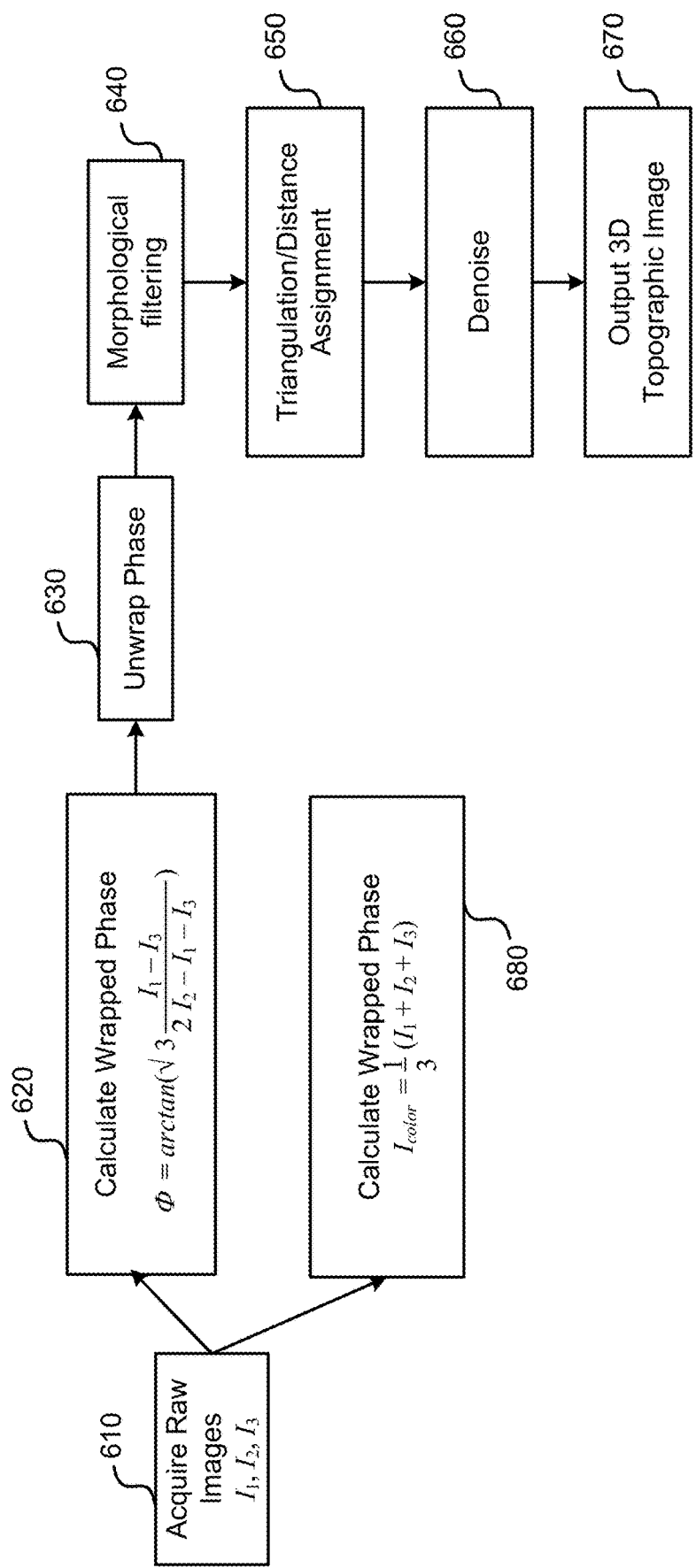
FIG. 6 shows a flowchart of another method for generating a 3D topographic image according to exemplary embodiments of the invention.

FIG. 6 shows a flowchart of another method for generating a 3D topographic image according to exemplary embodiments of the invention. This method may be used in conjunction with the system 200 shown in FIG. 2. In this example, the structured light pattern shown in FIG. 3 is a set of three sinusoidal patterns $I_1$, $I_2$, and $I_3$ that are phase shifted by 120 degrees with respect to each other. The sinusoidal patterns $I_1$, $I_2$, and $I_3$ are sequentially projected onto the surface of the sample 245 by the second light source 210. The sinusoidal patterns $I_1$, $I_2$, and $I_3$ may be represented as the following:

$$I_1 = I_0 + I_b \cos(kx - 2\pi/3) \tag{2}$$

$$I_2 = I_0 + I_b \cos(kx) \tag{3}$$

$$I_3 = I_0 + I_b \cos(kx + 2\pi/3) \tag{4}$$

As shown in FIG. 6, raw images of the sinusoidal patterns $I_1$, $I_2$, and $I_3$ are acquired at 610. In order to generate a 3D topographic image, a wrapped phase is calculated at 620. The wrapped phase may be calculated according to the following:

$$\varphi = \arctan\left(\sqrt{3}\, \frac{I_1 - I_3}{2I_2 - I_1 - I_3}\right) \tag{5}$$

The phase may then be unwrapped at 630. Morphological filtering may be performed at 640, and triangulation and/or distance assignment may be performed at 650. After denoising at 660, a 3D topographic image is output at 670.

Figure 7:
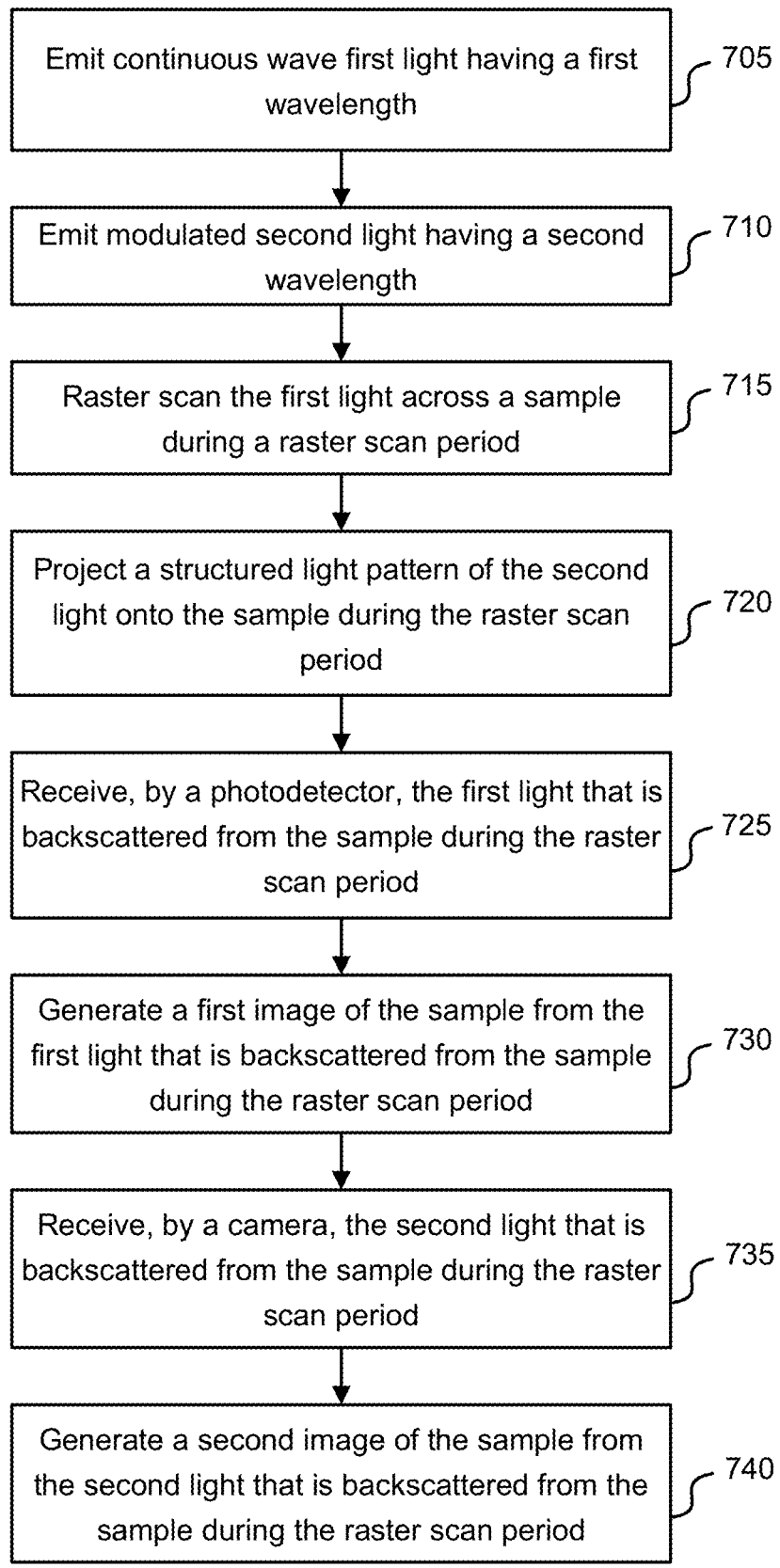
FIG. 7 shows a flowchart of a method for acquiring a plurality of images of a sample according to exemplary embodiments of the invention.

FIG. 7 shows a flowchart of a method for acquiring a plurality of images of a sample according to exemplary embodiments of the invention. As shown in FIG. 7, the method begins by emitting continuous wave first light having a first wavelength from a first light source at 705. The first wavelength may lie within the SWIR region of the spectrum. Modulated second light having a second wavelength is emitted from a second light source at 710. The second wavelength may lie within the visible or NIR region of the spectrum.

The first light is raster scanned across a sample by a scanning MEMS mirror during a raster scan period at 715. Meanwhile, a structured light pattern of the second light is projected onto the sample by the scanning MEMS mirror during the raster scan period at 720. An example of the synchronization between the first light and the second light is discussed above with regard to FIG. 3.

A photodetector receives at least a portion of the first light that is backscattered from the sample during the raster scan period at 725. A first image of the sample is generated from this light at 730. Meanwhile, a camera receives at least a portion of the second light that is backscattered from the sample during the raster scan period at 735. A second image of the sample is generated from this backscattered light at 740. The second image of the sample is a 3D topographic image of the sample. The first image of the sample and the second image of the sample may be output, such as to a display.

Specific details are given in the above description to provide a thorough understanding of the embodiments. However, it is understood that the embodiments can be practiced without these specific details. For example, circuits can be shown in block diagrams in order not to obscure the embodiments in unnecessary detail. In other instances, well-known circuits, processes, algorithms, structures, and techniques can be shown without unnecessary detail in order to avoid obscuring the embodiments.

Implementation of the techniques, blocks, steps and means described above can be done in various ways. For example, these techniques, blocks, steps and means can be implemented in hardware, software, or a combination thereof. For a hardware implementation, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed, but could have additional steps not included in the figure. A process can correspond to a method, a function, a procedure, a subroutine, a subprogram, etc. When a process corresponds to a function, its termination corresponds to a return of the function to the calling function or the main function.

Furthermore, embodiments can be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks can be stored in a machine readable medium such as a storage medium. A code segment or machine-executable instruction can represent a procedure, a function, a subprogram, a program, a routine, a subroutine, a module, a software package, a script, a class, or any combination of instructions, data structures, and/or program statements. A code segment can be coupled to another code segment or a hardware circuit by passing and/or receiving information, data, arguments, parameters, and/or memory contents. Information, arguments, parameters, data, etc. can be passed, forwarded, or transmitted via any suitable means including memory sharing, message passing, ticket passing, network transmission, etc.

For a firmware and/or software implementation, the methodologies can be implemented with modules (e.g., procedures, functions, and so on) that perform the functions described herein. Any machine-readable medium tangibly embodying instructions can be used in implementing the methodologies described herein. For example, software codes can be stored in a memory. Memory can be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" can represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes but is not limited to portable or fixed storage devices, optical storage devices, wireless channels, and/or various other storage mediums capable of storing that contain or carry instruction(s) and/or data.

While the principles of the disclosure have been described above in connection with specific apparatuses and methods, it is to be clearly understood that this description is made only by way of example and not as limitation on the scope of the disclosure.

What is claimed is:

1. A system comprising:
    a first light source that is configured to emit first light having a first wavelength as a temporally continuous beam;
    a second light source that is configured to emit second light having a second wavelength as a temporally modulated beam;
    a combiner that is configured to combine the first light and the second light along a single path;
    a scanning mirror that is positioned to receive the first light and the second light and configured to:
        raster scan the first light across a sample during a raster scan period, and
        project a structured light pattern of the second light onto the sample during the raster scan period;
    a photodetector that is configured to receive at least a portion of the first light that is backscattered from the sample during the raster scan period;
    a camera that is configured to receive at least a portion of the second light that is backscattered from the sample during the raster scan period; and
    one or more processors that are configured to:
        generate a first image of the sample from the at least the portion of the first light that is backscattered from the sample during the raster scan period,
        generate a second image of the sample from the at least the portion of the second light that is backscattered from the sample during the raster scan period, wherein the second image of the sample is a three-dimensional topographic image of the sample, and
        output the first image of the sample and the second image of the sample.

2. The system according to claim 1, wherein the first wavelength is between 900 nm and 1700 nm, and the second wavelength is between 380 nm and 900 nm.

3. The system according to claim 1, wherein the combiner comprises a wavelength-division multiplexer or a dichroic beam splitter.

4. The system according to claim 1, further comprising a third light source that is configured to project white light onto the sample before or after the raster scan period, wherein:
    the camera is further configured to receive at least a portion of the white light that is backscattered from the sample before or after the raster scan period, and
    the one or more processors are further configured to generate a third image of the sample from the at least the portion of the white light that is backscattered from the sample before or after the raster scan period, wherein the third image of the sample is a color image of the sample.

5. The system according to claim 1, wherein the structured light pattern of the second light comprises a Gray code pattern.

6. The system according to claim 1, wherein the structured light pattern of the second light comprises three sinusoidal patterns that are sequentially projected onto the sample and are phase shifted by 120 degrees relative to each other.

7. The system according to claim 6, wherein the one or more processors are further configured to calculate a third image of the sample from images of the sample generated by the three sinusoidal patterns, and wherein the third image of the sample is a color image of the sample.

8. The system according to claim 6, wherein the one or more processors are further configured to calculate the second image of the sample from images of the sample generated by the three sinusoidal patterns.

9. The system according to claim 1, further comprising a display that is configured to show the first image of the sample and the second image of the sample.

10. The system according to claim 1, wherein the photodetector is a single-pixel InGaAs photodetector.

11. A method comprising:
   emitting first light having a first wavelength as a temporally continuous beam;
   emitting second light having a second wavelength as a temporally modulated beam;
   combining the first light and the second light along a single path;
   directing the first light and the second light to a scanning mirror;
   raster scanning the first light across a sample during a raster scan period;
   projecting a structured light pattern of the second light onto the sample during the raster scan period;
   receiving, by a photodetector, at least a portion of the first light that is backscattered from the sample during the raster scan period;
   generating a first image of the sample from the at least the portion of the first light that is backscattered from the sample during the raster scan period;
   receiving, by a camera, at least a portion of the second light that is backscattered from the sample during the raster scan period;
   generating a second image of the sample from the at least the portion of the second light that is backscattered from the sample during the raster scan period, wherein the second image of the sample is a three-dimensional topographic image of the sample; and
   outputting the first image of the sample and the second image of the sample.

12. The method according to claim 11, wherein the first wavelength is between 900 nm and 1700 nm, and the second wavelength is between 380 nm and 900 nm.

13. The method according to claim 11, wherein combining the first light and the second light comprises using a wavelength-division multiplexer or a dichroic beam splitter.

14. The method according to claim 11, further comprising:
   projecting white light onto the sample before or after the raster scan period;
   receiving, by the camera, at least a portion of the white light that is backscattered from the sample before or after the raster scan period; and
   generating a third image of the sample from the at least the portion of the white light that is backscattered from the sample before or after the raster scan period, wherein the third image of the sample is a color image of the sample.

15. The method according to claim 11, wherein the structured light pattern of the second light comprises a Gray code pattern.

16. The method according to claim 11, wherein the structured light pattern of the second light comprises three sinusoidal patterns that are sequentially projected onto the sample and are phase shifted by 120 degrees relative to each other.

17. The method according to claim 16, further comprising calculating a third image of the sample from images of the sample generated by the three sinusoidal patterns, wherein the third image of the sample is a color image of the sample.

18. The method according to claim 16, wherein the second image of the sample is calculated from images of the sample generated by the three sinusoidal patterns.

19. The method according to claim 11, further comprising displaying the first image of the sample and the second image of the sample.

20. The method according to claim 11, wherein the photodetector is a single-pixel InGaAs photodetector.

* * * * *